United States Patent [19]

Tehon et al.

[11] 4,129,031
[45] Dec. 12, 1978

[54] IMMERSIBLE LIQUID DENSITOMETER

[75] Inventors: Stephen W. Tehon, Clay; Edward M. Pruski, Liverpool, both of N.Y.

[73] Assignee: General Electric Company, Syracuse, N.Y.

[21] Appl. No.: 833,733

[22] Filed: Sep. 16, 1977

[51] Int. Cl.² .............................................. G01N 9/00
[52] U.S. Cl. .................................................. 73/32 A
[58] Field of Search ................ 73/32 A, 32 R, 54, 59, 73/30

[56] References Cited

U.S. PATENT DOCUMENTS

| 2,518,348 | 8/1950 | Mason | 73/54 |
| 2,819,610 | 1/1958 | White | 73/59 |
| 3,225,588 | 12/1965 | Moulin et al. | 73/32 A |

*Primary Examiner*—James J. Gill

*Attorney, Agent, or Firm*—Richard V. Lang; Carl W. Baker; Frank L. Neuhauser

[57] ABSTRACT

An immersible liquid densitometer is disclosed employing an immersible vibrator. The vibrator includes one or two masses which are resiliently supported and which contain perforations which fill when the vibrator is immersed in the liquid. When the vibrator is immersed, the frequency of vibration is affected in proportion to the density of the liquid filling the perforations. Thus, measurement of the frequency of vibration may be used to determine the density of the immersing liquid. For maximum accuracy, the configuration and vibratory mode of the masses are selected for minimum energy coupling to the liquid. Typically, a cylindrical configuration is selected vibrating in a rotational mode. Under these conditions, the drag during vibration is due primarily to skin friction and a high Q, high accuracy measurement is achieved.

12 Claims, 3 Drawing Figures

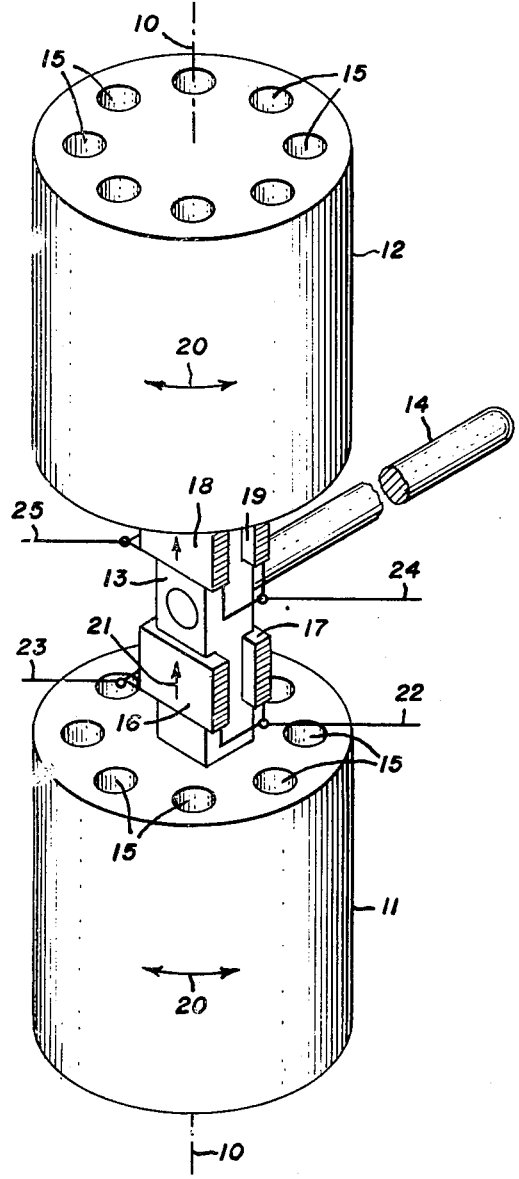
FIG.1.
FIG.2.
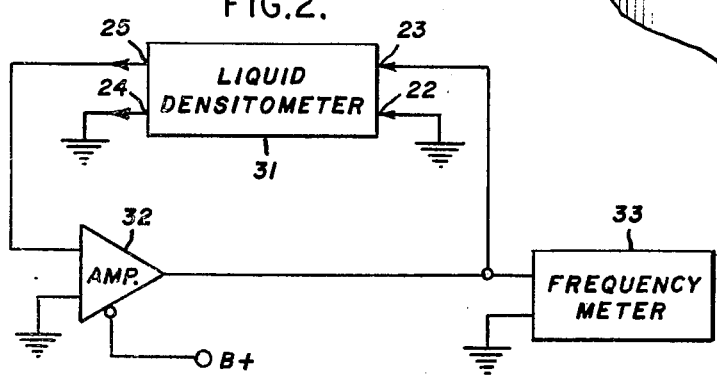
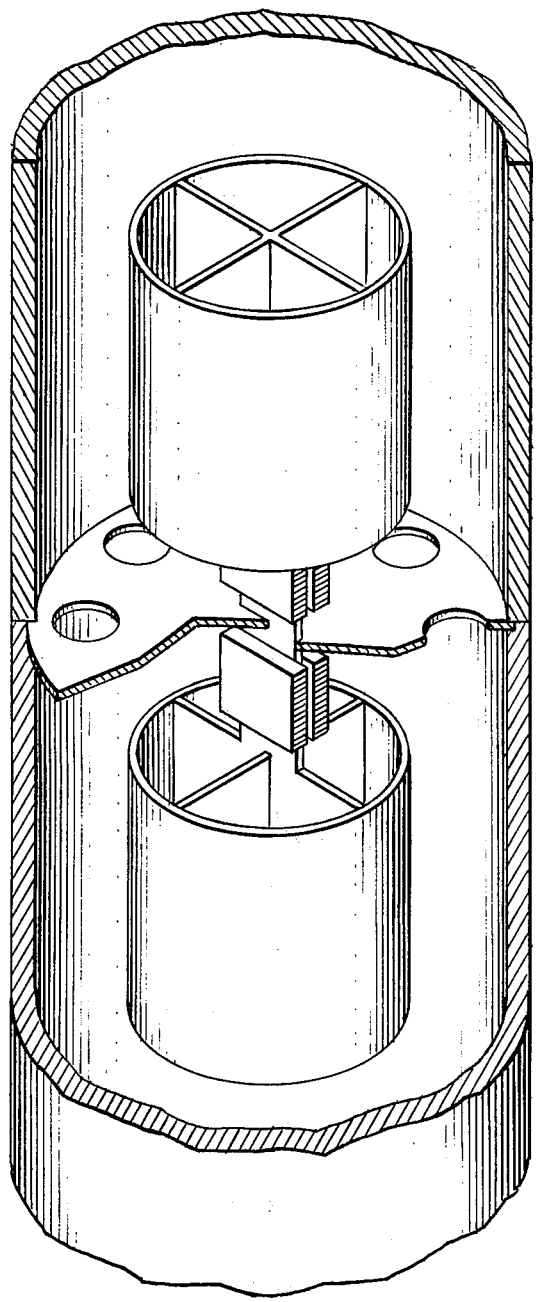
FIG.3.

IMMERSIBLE LIQUID DENSITOMETER

BACKGROUND OF THE INVENTION

1. Field of the Invention

The present invention relates to the measurement of the density and viscosity of a liquid and more particularly to a densitometer which may be immersed in a liquid to measure these properties.

2. Description of the Prior Art

Laboratory instruments are available which measure liquid density with appreciable accuracy, involving the careful weighing of known volumes of liquid with precision laboratory balances. In such instruments, the density is obtained by calculating the ratio of the weight of the liquid to the volume. Accurate hydrometers containing weighted floats and graduated walls are placed in the liquids being measured and the volume of liquid displayed is carefully measured along the graduations. Here the accuracy is on the order of a percent. Dynamic devices have been built employing the momentum exchange between a moving liquid and balanced beams. The output of such devices is an analog signal with accuracies on the order of $\frac{1}{4}\%$. A second dynamic measurement is by means of a tuning fork with tines into which liquid whose density is being measured is pumped. The frequency of vibration of the tuning fork has a higher value when empty and a lower value when filled with liquid. The variation in frequency is a function, in part, of the density of the liquid. Using a calibration technique, the density of the contained liquid may be obtained to accuracies on the order of one part in $10^3$ or $10^4$. The tuning fork method is relatively slow and discontinuous, requiring access to the tuning fork, and an emptying step. Should one wish to make continuous measurements, simple immersion is ruled out since the normal mode of vibration of a tuning fork produces turbulence and an extremely strong damping effect. Accuracy in the measurement of the resonant frequency of a resonant system is strongly dependent on the Q of the resonent system. Since excessive turbulence reduces the Q of the oscillator, the accuracy of measurement is greatly reduced. To avoid inaccuracy, non-turbulent resonance is essential.

SUMMARY OF THE INVENTION

Accordingly, it is an object of the present invention to provide an improved immersible liquid densitometer.

It is a further object of the present invention to provide an immersible liquid densitometer of improved accuracy.

It is another object of the present invention to provide an improved immersible dynamic liquid densitometer.

It is an object of the present invention to provide an improved device for measuring density and viscosity.

These and other objects of the invention are achieved in an immersible liquid densitometer which comprises a vibrator operating in a rotational mode and having a configuration selected with respect to that mode which, when the vibrator is immersed, produces a minimum drag by the liquid upon the moving parts of the vibrator, or which couples a minimum of mechanical energy from the vibrator to the surrounding liquid. The vibrator contains one of the two perforated masses supported on a torsionally resilient bar, the perforations allowing liquid to be admitted upon immersion. The admission of liquid causes the effective rotational moment of inertia of each mass to increase and thereby the vibrator frequency to decrease in accordance with the density of the admitted liquid. The densitometer further comprises means for measuring the resonant frequency of the vibrator to determine the density of the immersing liquid.

Each rotating mass has an exterior which substantially conforms to a surface of revolution about the selected axis of rotation, and which in the simplest case is cylindrical. A cylindrical mass rotating on its axis in a liquid has the property of exhibiting purely tangential motion at the solid liquid interface, a property which reduces any surface displacement normal to the surrounding liquid to a minimum. The drag or energy loss that occurs during vibration is due primarily to skin friction, and primarily to that part of skin friction accompanying laminar flow or viscous drag.

The perforations, in one practical form, take the form of a plurality of circular holes, oriented parallel to the axis of the cylindrical mass, and disposed near the outside wall. The holes enter the cylindrical mass at one planar end surface and exit at the other planar end surface. Any liquid admitted into the holes in constrained by the side walls of the holes to rotate together with the masses, and thus adds to the effective rotational moment of inertia of the vibrator in proprtion to the density of the liquid.

In a second practical form, each of the rotating masses is formed of a thin cylinder open at each end and containing a plurality of vanes, extending radially from the axis of the cylinder to the outside wall of the cylinder. When the mass rotates, the vanes constrain the trapped liquid to rotate with the mass, and increase the effective rotational moment of inertia of the vibrator in proportion to the density of the liquid.

In both of the above practical arrangements, the perforations begin and end at the end surfaces of the cylinder and the end faces are designed, by an essentially straight cut off construction, for a minimum of drag in a rotational motion. In both practical arrangements, the openings of the ends are alike, the natural consequence of which is to prevent any preference of one end over the other for admitting or discharging liquid. Both designs sustain an ideally trapped liquid condition. In a third practical arrangement, where bubbles tend to settle on stagnant surfaces, a small degree of pumping may be provided to purge bubbles from the interior of the perforations. In modifying the first arrangement, this pumping is done by making the aperture entrances at one end at a shorter radius from the axis than at the other end. The effect is to progressively discharge liquid at the end of the apertures at a greater radial distance from the axis.

The total drag losses of the vibrator, using the bored cylindrical design corresponds to a virtual Q of over 900 (in kerosene). In many applications, the liquid drag represents a lower order of losses than the other losses of the resonator. Two pairs of piezoelectric transducers serve respectively to excite and detect torsional vibration. The second pair, which detects torsional vibration, is connected to frequency sensing equipment.

BRIEF DESCRIPTION OF THE DRAWINGS

The novel and distinctive features of the invention are set forth in the claims appended to the present application. The invention itself, however, together with further objects and advantages thereof may best be understood by reference to the following description and accompanying drawings, in which:

FIG. 1 is a drawing of an immersible liquid densitometer using a vibrator whose frequency is a measure of the density of the immersant liquid and which uses a pair of cylindrical masses containing a plurality of circular holes to trap the immersant liquid and produce dependent alteration in vibrator frequency;

FIG. 2 is a block diagram of a densitometer measurement system including input and output transducers associated with the vibrator, an amplifier, and a frequency meter, the measured oscillation frequency indicating the density of the immersant liquid; and FIG. 3 is a variant construction in which each mass takes the form of a cylinder open at both ends and containing a plurality of internal vanes dividing its interior into axially extending sections.

DESCRIPTION OF THE PREFERRED EMBODIMENTS

An immersible liquid densitometer in accordance with the invention is shown in FIG. 1. It comprises a vibrator, which vibrates at a frequency which is a function of the density of the liquid in which it is immersed and means (not fully illustrated in FIG. 1) for measuring the resonant frequency of the vibrator to obtain the density measurement.

The vibrator consists of a first generally cylindrical mass 11, a second generally cylindrical mass 12, an elongated torsionally compliant bar 13, two pairs of shear transducers 16, 17 and 18, 19, and a support 14. The three elements 11, 12 and 13 are aligned coaxially along the axis 10 and torsional vibration is produced as illustrated by the arrows 20. As the arrows imply, the vibration is one in which the masses 11 and 12, which may be regarded as rigid bodies, rotate in an oscillatory fashion about the axis 10, while the twisting support required for this motion is provided by the torsionally compliant bar 13. The normal mode of vibration is one in which the mass (e.g. 11) rotates counterclockwise while the other mass (e.g. 12) rotates clockwise, and then vice versa.

The twisting mode of rotation is achieved by designing the bar 13 for high compliance in an axial twist, suitable excitation by the driver transducers 16 and 17, and by a suitable nodal support 14. In a practical construction of the FIG. 1 embodiment, assuming that it is not temperature compensated, the masses 11 and 12, and the compliant bar may be fabricated from a monolithic piece of metal, for instance brass. The compliance of the mid-section is a function of its reduced cross section ($\frac{1}{8}$ inch $\times$ $\frac{1}{8}$ inch) in relation to the relatively larger cross section (1 inch diameter) of the masses. The driver transducers are mounted on the compliant bar 13 below the support 14 (as seen in FIG. 1), near to the mass 11. The driver transducers operate as a symmetrical pair in that each transducer generates a pair of shearing stresses. The four shearing stresses, as will be described below, form two counter-rotating torque couples, spaced apart by the width of the transducers (measured along the axis 10). The torque couples generate a twisting strain in a short axial section of the bar 13 which propagates along the bar and produces a general torsional vibration of the bar. The center of the compliant bar, mid-way between the ends, is at a nodal position in respect to this rotational vibration and provides a support point for the densitometer which diverts no vibrational energy into the supporting structure. Frequency measurement is achieved by a second pair of transducers 18 and 19 mounted on the resilient bar 13 above the support 14 (as seen in FIG. 1) and near to the mass 12. These transducers act as sensors of the torsional vibration.

A major feature is the provision of a plurality of perforations 15 in the masses 11 and 12 which fill with liquid upon immersion, allowing the trapped liquid to increase the effective rotational moment of inertia of the vibrator. The perforations are normally oriented in a vertical direction when the densitometer is in operation. When the device is immersed in the liquid with some inclination toward the vertical, any air in the circular perforations 15 will be expelled upward due to its buoyancy and immediately replaced with the immersing liquid. The perforations are oriented parallel to the axis of the individual masses and at a nearly maximum radial distance from the axis of rotation for maximum effect on the total moment of inertia. When rotational vibration of the masses is initiated, some radial restraint to transfer the rotational component of motion from the mass to the trapped liquid is necessary. The walls of the circular perforations 15 act as the radial restraints forcing the trapped liquid to rotate in synchronism with the masses. Assuming that the trapped liquid rotates in synchronism with the masses, then a readily calculated increase in the total rotational moment of inertia of each half of the vibrator will take place. If only air fills the perforations or the device is in a vacuum, the rotational moment of inertia is smallest and the resonant frequency is highest. As denser and denser liquids fill the perforations, the resonant frequency falls as the total moment of inertia increases. Measurement of the resonant frequency of the vibrator is then used to accurately measure the density of the liquid in which it is immersed. Accuracies on the order of 0.1 percent are readily achieved.

The transducers illustrated in FIG. 1 are of a piezoelectric ceramic typically of lead zirconate titanate (PZT 5H) electroded to couple shear strains to the torsionally compliant bar. The visible transducer 16, for instance, has its body polarized axially upward as indicated by the arrow 21, while the nearly hidden transducer 17 has its body polarized axially downward. The right edge (as disposed in FIG. 1) of the bodies of transducers 16 and 17 are electroded and coupled to a common lead 22. Similarly, the left edges (as disposed in FIG. 1) of the bodies of the transducers 16 and 17 are electroded and coupled to a common lead 23. From this it may be seen that any electric field established between leads 22 and 23 is orthogonal to the polarization vectors of transducers 16 and 17, and will produce a rhombic or a parallelogrammatic distortion of the transducer. In this distortion, one pair of diagonal corners may be regarded as being pushed apart and the other pair of diagonal corners as being drawn together. Since the bodies of the transducers 16 and 17 are oppositely polarized, the leads 22 and 23, which couple the same polarity of field between the right and left electrodes produce mutually opposite shear strains in the two transducers. Thus, the diagonal corner pair experiencing a drawing together in the hidden transducer 17 are adjacent to diagonal corner pair experiencing a pushing apart in the exposed transducer 16. Thus, a torque couple is created between the upper edges of the two transducers, which tends to twist the cross section of the bar 13 in a clockwise direction. At the same time an oppositely directed torque couple is created between the lower edges of the two transducers which tends to twist the cross section of the bar 13 in a counterclockwise direction. The two couples just described act through the bonds between the transducer and the small section of the bar embraced by the upper and lower limits of the transducers, and create a localized torsional strain in the bar. Assuming an alternating excitation, each diagonal corner pair of transducers alternately draws in and pushes out, and each couple alternates between a clockwise and a counterclockwise twist. Thus, the torsional twist in the bar 13 alternates with each field reversal between a progressively more clockwise twist (as one progresses upward along the axis of the bar) and a progressively more counterclockwise twist. Assuming an influx of energy adequate to sustain resonance and of appropriate frequency, the localized strain will propagate throughout the compliant region of the bar, and cause an oscillatory rotation of the two masses 11 and 12 attached to the ends.

The vibrator, whose motion has just been described, may be regarded as having a natural resonant frequency which is dependent on the immersing medium. The resonant frequency may be determined in a number of ways. The sensor of the vibratory motion induced by the driver transducers 16 and 17 is the pair of sensor transducers 18 and 19, earlier mentioned. Due to the reciprocal nature of the piezoelectric process, the sensor transducers 18, 19 may be identical to the driver transducers 16, 17. They will undergo corresponding rhombic or parallelogrammatic strains like the driver transducers and at their output, an alternating voltage comparable in certain respects to the input voltage applied to the driver transducers will appear. This output voltage is derived by the leads 24 and 25. Lead 24 is coupled to the right electrodes of the sensors 18, 19 and the lead 25 is coupled to the left electrodes of sensors 18, 19 (using the orientations of FIG. 1).

Prior to further discussion of the electrical system coupled to the driver and sensor transducers, a discussion of the hydraulic design of the resonator will be undertaken.

The primary element in the hydraulic design is the selection of a mode of vibration in which cylinders rotate on their cylindrical axes. The effect of this choice of mode is that elements of the cylindrical masses (11, 12) move to new positions without requiring any elemental surface motion normal to the surrounding liquid. Thus, no liquid is displaced. Assuming no perforations or interruptions in the cylindrical surface, the only effect upon the immersing liquid of rotational motion of a cylinder, since no liquid is displaced, is tangential motion which occasions viscous or surface drag. Since liquids have no shear strength, offering only a small resistance or surface drag, the torsional resonator rotates with only a small damping effect. The damping is due to the viscosity of the liquid and surface adhesion. In general, the damping is more evident in highly viscous liquids, such as heavy oil rather than "light" liquids such as kerosene and freon.

Viewed mathematically, since the liquid cannot support an elastic shear, there is no reactive term in the equation of motion due to the hydraulic forces upon the cylinder but only a resistive term. Had there been a reactive term, the frequency of vibration would have been directly affected by the hydraulic properties of the liquid. With only a resistive term, the frequency of vibration is essentially unchanged by the hydraulic properties of the liquid. As a result, such properties as the viscosity of the liquid increase or decrease the amount of energy required to sustain oscillation but have only a small affect on the frequency of oscillation. Thus, assuming the cylinder is without perforations, it may be immersed in a liquid, and the frequency will not change more than one part in $10^5$ — but the Q which is a measure of energy absorption, may be substantially reduced.

With the perforations, the resonator design must facilitate the trapping of a readily ascertained amount of liquid in the perforations of each rotating mass and the design of the perforations should produce a minimum of energy coupling to the surrounding liquid. The use of a plurality of relatively small holes as illustrated in FIG. 1 opening at the two planar end walls of the cylindrical masses, has been found to be a particularly effective design in producing a minimum of pumping and for holding the energy coupling to the surrounding liquid to a minimum. When the holes are parallel to the axis 10, the rotational motion produces essentially no pumping effect and the bulk of the liquid trapped in the holes has no inclination to move out either opening. At the same time, the surrounding liquid in contact with the end surfaces of the mass 11 and 12 abuts the planar end of the surface with small liquid filled holes. The edges of the holes should avoid scooping and are preferably cut off squarely. The net effect is that a resonator which has a natural Q of 220 in air may have a Q of 180 in kerosene. Significantly, the kerosene may be calculated from the above measured values for Q as having an equivalent Q of 960. This implies that the natural loss of mechanisms operating on a resonant bar in air such as wind resistance, generation of heat from resistance in the wires, friction in the ceramic, etc. are much larger than the loss produced by immersion of the system in kerosene.

The practical arrangement illustrated in FIG. 1 has been drawn approximately to scale with the cylindrical elements being approximately 1 inch in diameter and 1 inch in length. The resonant frequency achieved is near 800 Hertz and the amplitude of vibration on the order of several thousandths of an inch and while not visible to the eye is sensible to the touch.

The complete densitometer measurement system is illustrated in FIG. 2 in an electrical block diagram. It comprises the densitometer bearing the reference numeral 31, the amplifier 32 and frequency meter 33. The densitometer 31 may be the device shown in either FIG. 1 or FIG. 3 and is illustrated as a block having two electrical connections 22 and 23 representing electrical input connections and two electrical connections 24 and 25 representing electrical ouptut connections. The reference numerals 22 through 25 correspond to those assigned in FIG. 1 to the connections to the densitometer. The electrical output connection 25 of the densitometer is applied to one input of a wide band amplifier 32. The other input of amplifier 32 is grounded as are the connections 22 and 24. The output of the amplifier 32 is coupled to the electrical input connection 23 of the densitometer. The amplifier has an electrical connection for d.c. energization.

The measurement system of FIG. 2 functions in the following manner. The densitometer is interconnected with an amplifier in such a manner that the densitometer provides a regenerative feedback connection from the output to the input of the amplifier. If adequate amplifier gain in present to achieve a loop gain in excess of unity, the network will oscillate. The frequency of oscillation of the network is the resonant frequency of the densitometer. If the loop gain is substantially in excess of that required for unity loop gain, the oscillatory condition becomes more stable. In addition, the presence of additional gain makes up for any insertion loss when the densitometer is immersed in lossy liquids. The frequency meter 33 is provided, coupled to the output terminal of the amplifier 32 for measuring the oscillation frequency. Since the frequency is dependent on the density of the liquid, the frequency reading may be converted to density.

The device may also be calibrated for viscosity measurement. The characteristic is not precisely linear, nor is it unaffected by the density of the liquid. The method for obtaining the viscosity is to measure the natural resonance frequency ($f_0$) of the vibrator, and then measure the frequencies ($f_1$, $f_2$), at which the resonant output is reduced 3 db to 0.707 of the maximum voltage. This leads to the "Q" of the vibration, which in turn is dependent on the ratio of the effective mass of the rotating cylinder (L) to the mechanical resistance (R):

$$Q = f_0/(f_2 - f_1) = \omega_0 L/R$$

The mechanical resistance term is approximately proportional to the viscosity of the liquid but may be calibrated for more accuracy.

For either density or viscosity measurement, the input transducers may be driven by power from a tunable oscillator, while the voltage induced by motion in the output transducers is connected to a voltmeter. Resonance is located by tuning the oscillator to the frequency for which the output voltage is a maximum. The exact frequency is then measured with a frequency meter connected to the output of the drive oscillator. The variation of output voltage with frequency is the function noted above for a single tuned resonant circuit.

A second embodiment of the invention is shown in FIG. 3. In this embodiment, the rotating masses each take the form of a short length of cylindrical tubing into which a four vane paddle is inserted. One pair of vanes in one cylinder is formed of a single piece of sheet metal and a second pair of vanes is attached at right angles to the first vane by a soldering or brazing process. Preferably, the sheet used for constructing the first pair of vanes is used to form the resilient bar, supporting the two cylinders, and to form the first two vanes of a second resonator. The second resonator is constructed similarly to the first and the third and fourth vanes welded along the mid-section at right angles to the first two. The sheet in the region supporting the rotating masses is of reduced width to provide an increased torsional compliance. In the illustrated application, the outer diameter of the cylinder is from ¼ inch to ½ inch and the width of the reduced resilient portion is from one quarter to one third the o.d. of the cylinder. The two transducer pairs are applied to the reduced section of the central sheet and are typically ⅛ inch × ⅛ inch or ¼ inch × ¼ inch.

The foregoing arrangement of FIG. 2 has the advantage of increasing the ratio of the empty rotational mass of the rotating cylinder to the immersed rotational mass (in which liquid is trapped). Thus, the arrangement illustrated in FIG. 1 produces approximately 5% change in resonant frequency between operation in air and immersed in kerosene, while the FIG. 2 embodiment is designed to produce a change in resonant frequency of approximately 25%.

Either of the arrangements of FIG. 1 or FIG. 2 may be designed to achieve temperature stability. In both cases, since the resonator may be viewed as a pair of lumped masses acting in combination with a lumped spring member, a compensation for each property produces a high degree of temperature compensation. More particularly, the rotational moment of inertia of the masses may be held stable to a high degree of accuracy against temperature variation by fabrication of the mass of Invar, Nilvar or fused quartz. This holds the dimensions of the mass constant throughout the range of temperature compensation. Simultaneously, one may stabilize the elastic modulus of the compliant bar. Suitable materials for the bar are Ni-Span C, Elinvar or Elinvar-Extra. A more cumbersome mode of temperature compensation may be employed by using a resonator as a standard without holes and one with holes and then making a frequency comparison between the two.

While both embodiments have employed a matched pair of resonators, one may also use a single ended resonator in which the resilient bar is supported on a large rigid mass and the other rotating mass is eliminated. While it is theoretically impossible to remove all vibration from the support, the amount remaining may be small, and practical single ended operation may be achieved. In the single-ended case, one may either use a single pair of resonant transducers or two pairs of transducers for the driving and the sensing functions.

In addition, while resonant operation has been achieved through the use of piezoelectric transducers, such transducers are of relatively high electrical impedance and may require relatively high operating voltages, thus, giving rise to the possibility of occasional sparks which might create a fire hazard. Where avoidance of the fire hazard is essential, a lower voltage magnetic drive may be used.

At low amplitudes of motion, dissipation within the densitometer structure is a constant fraction of the stored energy, both in elastic deformation of the resilient spring member and in the motion of the end masses. In a vacuum, or essentially in air, the ratio of stored energy to dissipated power defines the mechanical Q of the device. Equivalently, the reciprocal of Q is the fractional part of energy which is dissipated. Insertion of the device into an immersing liquid increases the dissipation fraction, corresponding to a decrease in Q. We have found in experiments with the torsional densitometer, that the fractional increase in dissipation, due to immersion, is independent of the amplitude of vibration, and that this portion of dissipation is a small part of the total fractional dissipation within the device. We also observe a further moderate increase in dissipation, and corresponding decrease in Q, if a more viscous immersion liquid is used. The small amount of dissipation into the immersing liquid is responsible for the high efficiency in this form of densitometer, which permits accurate measurement of density at low amplitudes of vibration. If this high efficiency had not been achieved, higher amplitudes of motion, and in general reduced accuracies due to reduced Q, would have been encountered. It would be expected that higher amplitudes of motion would produce lower Q operation due to nonlinear dissipation in the immersing liquid.

The key to reduced excursion and high Q ia avoidance of motion normal to the surface forming the solid-liquid interface. Therefore, the use of torsional motion, with a surface of revolution, provides the optimum conditions for low loss under immersion.

In application to density of aircraft fuel, the usual existence of high electromagnetic interference makes measurements with wide band devices difficult. The narrow band operation in this form of densitometer is a distinct advantage, since interference outside the narrow band of measurement has no effect.

What is claimed as new and desired to be secured by Letters Patent of the United States is:

1. An immersible liquid densitometer comprising:
    A. a vibrator which vibrates in torsion about a predetermined axis comprising:
        (1) a pair of symmetrical masses having equal rotational moments of inertia and exteriors substantially conforming to a surface of revolution about said axis to permit tangential surface motion and to preclude substantial surface motion normal to the surrounding liquid during torsional vibration to minimize energy coupling to the surrounding liquid, said masses containing self-filling perforations which admit liquid upon immersion, and which are designed to cause said admitted liquid to rotate with the masses to form effective rotational moments of inertia as a function of both the mass and the admitted liquid, said perforations being symmetrical to cause said effective rotational moments of inertia to remain equal,
        (2) a resilient member supporting said masses symmetrically at the respective ends thereof in said torsional vibration mode, said resilient member being itself supported midway between the ends, at the node of said torsional vibration, and
        (3) means for exciting said torsional vibration, and
    B. means coupled to said vibrator for measuring the resonant frequency thereof to determine the density of the liquid in which said vibrator is immersed.

2. A densitometer as in claim 1 wherein the edges of the openings of said perforations lie in said surface of revolution to minimize energy coupling in the surrounding liquid.

3. A densitometer as set forth in claim 2 wherein said peforations are oriented in a direction having a substantial vertical component to facilitate easy entry of a liquid and easy expulsion of gas to avoid trapping gas bubbles.

4. A densitometer as set forth in claim 3 wherein the opening of each perforation in one end is at a shorter radius from the torsional axis than the opening at the other end, to facilitate a slow pumping of the liquid through the perforation when vibration occurs.

5. A densitometer as set forth in claim 3 wherein the interiors of said perforations form a smooth path from one opening to the other to prevent the trapping of gas bubbles.

6. A densitometer as set forth in claim 2 wherein said masses are substantially cylindrical with planar end surfaces, and said perforations traverse said masses having openings whose edges lie in said end surfaces.

7. A densitometer as set forth in claim 6 wherein said mass is cylindrical, and wherein
    said perforations are a plurality of circular holes oriented parallel to the axis of the cylindrical mass and disposed near the wall thereof.

8. A densitometer as set forth in claim 6 wherein said mass is cylindrical and consists of a thin cylinder open at both ends and containing a plurality of vanes extending radially from the axis of the cylinder to the wall thereof, said perforations having a sector shaped cross section.

9. A densitometer as set forth in claim 1 wherein:
    A. said masses are formed of a material having a zero temperature coefficient of expansion, and
    B. said resilient member is of a material having an elastic modulus with a zero temperature coefficient.

10. An immersible liquid densitometer as in claim 1 wherein said means for exciting said torsional vibration is a piezoelectric transducer bonded to said resilient member and itself vibrating in torsion.

11. An immersible liquid densitometer as in claim 10 wherein said means for exciting said torsional vibration is a pair of piezoelectric transducers bonded to opposite surfaces of said resilient member to effect a torsional couple acting about said rotational axis.

12. An immersible liquid densitometer as in claim 11 wherein said frequency measuring means comprises a second pair of piezoelectric transducers, each transducer pair being equidistant from and on opposite respective sides of the nodal support.

* * * * *